United States Patent [19]

Okumura et al.

[11] Patent Number: 5,378,783
[45] Date of Patent: Jan. 3, 1995

[54] DICYCLOPENTADIENE ACTIVATION METHOD AND POLYMERIZATION COMPOSITION

[75] Inventors: Kin-ichi Okumura, Kamakura; Masao Torii, Kurashiki; Hirotoshi Tanimoto, Ayase; Motoyuji Yamato, Naka, all of Japan

[73] Assignee: Nippon Zeon Co., Ltd., Tokyo, Japan

[21] Appl. No.: 704,550

[22] Filed: May 23, 1991

[30] Foreign Application Priority Data

May 23, 1990 [JP] Japan .................................. 2-133644

[51] Int. Cl.⁶ ............................................ C08G 61/08
[52] U.S. Cl. ..................................... 526/283; 526/77; 526/161; 526/282; 585/22; 585/851; 585/852; 585/853; 585/855; 203/6; 203/9
[58] Field of Search ........................ 526/77, 283, 282; 585/22, 851, 852, 853, 854, 855

[56] References Cited

U.S. PATENT DOCUMENTS

| | | |
|---|---|---|
| 4,426,502 | 1/1984 | Minchak . |
| 4,584,425 | 4/1986 | Tom . |
| 4,882,401 | 11/1989 | Bell .................................. 526/283 X |
| 4,943,621 | 7/1990 | Janda et al. ...................... 526/283 X |
| 4,977,226 | 12/1990 | Sugawara et al. .................. 526/283 |
| 5,082,909 | 1/1992 | Bell .................................. 526/283 X |

FOREIGN PATENT DOCUMENTS 0139170 5/1985 European Pat. Off. .
0180362 5/1986 European Pat. Off. .

OTHER PUBLICATIONS

Hackh's Chem. Dictionary, J. Grant (ed.), McGraw-Hill, Inc., N.Y., p. 26 (1969).
Patent Abstracts of Japan, vol. 13, No. 308 (C-617) [3656], Jul. 14, 1989—"Purification of Dicyclopentadiene" by Munetoshi Nakano, Nippon Zeon Co. Ltd.

*Primary Examiner*—Fred Teskin
*Attorney, Agent, or Firm*—Thoburn T. Dunlap

[57] ABSTRACT

A highly polymerizable dicyclopentadiene (DCPD) monomer composition is obtained. The dicyclopentadiene so obtained is highly suitable for ring-opening polymerization by metathesis catalysts. The active DCPD yields articles with excellent physical properties upon in-mold polymerization.

15 Claims, No Drawings

DICYCLOPENTADIENE ACTIVATION METHOD AND POLYMERIZATION COMPOSITION

BACKGROUND OF THE INVENTION

1. Technical Field

The present invention relates to a polymerizable monomer feed composition and methods for the polymerization thereof. More particularly, the invention pertains to the economical manufacture of dicyclopentadiene which has a high polymerization activity suitable for reaction injection molding in the presence of a metathesis catalyst.

2. State of the Art

Cycloolefins have been in-mold bulk polymerized via metathesis ring-opening polymerization to obtain molded articles having desirable physical properties. The polymerization reaction is catalyzed by a two part metathesis catalyst system. One part contains a tungsten or molybdenum catalyst and the other part contains an organoaluminum cocatalyst.

A reaction injection molding (RIM) process has been commercially employed to obtain in-mold polymerized articles. RIM involves mixing at least two low viscosity reactive monomer streams and injecting the combined streams into a mold where the monomer quickly polymerizes into a solid polymeric article of a desired configuration. One of the monomer streams contains the catalyst component, while the other monomer stream contains the cocatalyst component.

Dicyclopentadiene (DCPD) can be polymerized in such a manner resulting in a product with very desirable physical properties. A problem that has been encountered in carrying out such polymerization reactions is that contaminates and impurities present in commercially available DCPD monomer inhibit the polymerization reaction by inhibiting the metathesis catalyst system. Commercially available DCPD monomer has a purity of about 95%, and satisfactory molded products cannot be obtained from such DCPD. Accordingly commercially available DCPD must be purified in order to prevent impurities from inhibiting the polymerization reaction.

Many purification methods have been suggested, such as treating DCPD with molecular sieves, alumina, or silica as disclosed in U.S. Pat. No. 4,584,425. Contacting DCPD with an alkaline compound, or heat treating DCPD have been disclosed in Japanese Kokai applications HEI 1-96140 and SHO 63-234017, respectively. However, these methods do not improve the degree of polymerization sufficiently. Even a highly purified DCPD monomer that contains a small amount of polymerization inhibiting components lead to reduced polymerization activity and an unstable polymerization reaction. Hence, a simple and effective method for deactivating such polymerization inhibiting components is needed.

SUMMARY OF THE INVENTION

It is a primary object of the present invention to provide a highly polymerizable DCPD monomer composition.

It is another object of the invention to provide a highly polymerizable reaction composition for RIM applications.

A further object is to provide a method for increasing the polymerization activity of a DCPD monomer solution.

A still further object is to provide a stable polymerization reaction for bulk polymerization of a DCPD monomer.

Another object is to provide a polymer prepared from a highly polymerizable monomer composition.

Still another object is to provide a metathesis polymerizable reactant composition comprising DCPD, at least one norbornene type monomer, a reducing agent, and a catalyst.

A further object is to provide a metathesis polymerizable reactant composition comprising DCPD, at least one other norbornene type monomer, a reducing agent, and a cocatalyst.

A still further object is to provide a metathesis polymerizable feed composition comprising DCPD, at least one other norbornene type monomer, a reducing agent, a catalyst, and cocatalyst.

These and other objects are accomplished by preparing a highly polymerizable DCPD composition by contacting DCPD with a reducing agent that selectively reacts with and inactivates the polymerization inhibiting components contained therein. The composition so obtained can be bulk polymerized in the presence of a metathesis catalyst system.

These features and advantages of the invention will appear in the description that follows and will be otherwise apparent to those skilled in the art.

DESCRIPTION OF THE INVENTION

Dicyclopentadiene

The crude DCPD utilized as the starting material in this invention may exist as the endo-isomer, the exo-isomer or mixtures thereof. Dicyclopentadiene is typically obtained by dimerizing cyclopentadiene from the carbon 5 fraction ($C_5$) of naphtha cracking and isolating the crude DCPD product by distillation. The purity of such crude DCPD is commonly at least about 90 weight % DCPD. The preferred purity for RIM applications should be no less than 94 weight %.

The other components contained in crude DCPD include oxygen-containing compounds (which are produced by oxidation when DCPD is exposed to air) such as peroxides, hydroxides, carbonyl compounds, and epoxy compounds. Still other components include hydrocarbons with 4 to 6 carbons; codimers of cyclopentadiene with butadiene, isoprene, or piperylene (vinylnorbornene, isopropenylnorbornene, propenylnorbornene, methylbicyclononadiene, and the like); trimers of cyclopentadiene; and compounds having acetylenic triple bonds such as 5-propyne-2-norbornene.

Among these, the oxygen-containing compounds and the acetylenic compounds are believed to be inhibitors of metathesis catalytic polymerization.

Reducing Agents

To inactivate the polymerization inhibitors, DCPD is contacted with at least one reducing agent selected from the following groups of metal-based and metal-compound-based compounds:

(1) alkali metals such as lithium or sodium and the like;

(2) metal hydrides such as lithium hydride, sodium hydride, or lithium aluminum hydride and the like;

(3) organoalkali metal compounds such as methyllithium, ethyllithium, n-propyllithium, n-butyllithium, sec-butyllithium, cyclohexyllithium, phenyllithium, benzyllithium, phenylsodium, benzylsodium, naphthalenesodium, triphenylmethylsodium, phenylpotassium, butadienepotassium, styrenepotassium, naphthalenepotassium, cyclopentadienylsodium, lithium enolate, sodium enolate, and the like;

(4) organoalkaline earth metal compounds selected from diethylmagnesium and dibutylmagnesium;

(5) Group IIB organometal and organometal halide compounds selected from diethylzinc, dimethylzinc, dibutylzinc, methylzinc iodide, ethylzince iodide, n-propylzinc iodide, dimethylcadmium, diethylcadmium, dibutylcadmium, and diphenylcadmium;

(6) Group IIIA organometal compounds such as triethylboron, trimethylaluminum, triethylaluminum, triisobutylaluminum, tricyclohexylaluminum, diethylaluminum chloride, ethylaluminum sesquichloride, ethylaluminum dichloride, diethylethoxyaluminum, and the like;

(7) Group IVA organic compounds such as tetraethyl silicate, triethyl hydrogen silicate, hydrogen tributyltin, dibutyllead, and the like; and (8) Grignard reagents such as methylmagnesium chloride, ethylmagnesium chloride, ethylmagnesium bromide, n-butylmagnesium chloride, butylmagnesium iodide, phenylmagnesium chloride, vinyl magnesium chloride, arylmagnesium chloride, and the like.

The foregoing reducing agents can be used singly or as a mixture of two or more. Diethylzinc, Grignard reagents, and n-butyllithium are preferred to the organoaluminum compounds because of their high reducing activity.

It is believed that the reducing agents of the invention react selectively with the metathesis polymerization inhibiting components, i.e., the oxygen-containing and acetylenic compounds and converting these inhibitors to compounds which are inert to the polymerization reaction. Hence, the polymerization activity of crude DCPD is increased.

The amount of reducing agent employed commonly ranges from about 0.005 to about 1.0 weight % based on crude DCPD. Preferably the amount of reducing agent employed ranges from about 0.01 to about 0.5 weight %. When the amount of reducing agent employed is too low, the improvement in the metathesis polymerization reaction is not pronounced. On the other hand, when an excessive amount is used, the DCPD may polymerize during the purification process.

The reducing agents can be used neat (i.e., dissolved directly in the DCPD monomer), or can be dissolved in a hydrocarbon solvent or polar organic solvent and then dispersed in the monomer. The concentration of reducing agent in the solvent commonly ranges from about 1 to about 30 weight % (based on the solvent). Examples of suitable solvents are hexane, petroleum thinner, toluene, tetrahydrofuran, and the like.

Monomer Activation

The activation of crude DCPD is accomplished by mixing a reducing agent (neat or in solvent) of the present invention in the crude DCPD at about 30° to about 120° C., preferably about 30° to about 100° C., for about 10 minutes to about 2 hours, preferably for about 10 minutes to about one hour, with stirring.

After mixing, an activated monomer composition comprising DCPD, unreacted reducing agent(s), a reducing agent solvent (if employed), and the reaction products of the reducing agent(s) and the metathesis polymerization inhibiting components is obtained. This composition can be used directly in a RIM process or the unreacted reducing agent(s), solvent, and reaction products can be separated from the activated monomer. These elements can be separated by well-known separation techniques such as, for example, water washing, adsorption, or distillation. Distillation is the preferred practice.

Distillation can be carried out at $-750$ to $1,000$ mmHg, preferably under vacuum at $-700$ to $-200$ mmHG, at a bottoms temperature of about 60° to about 130° C., and preferably about 80° to about 110° C.

A packed distillation column large enough to avoid splashing of the bottoms liquid is employed for the distillation process. To avoid the formation of deleterious polymerization inhibitors during the distillation process, distillation preferably should be carried out in the presence of an antioxidant. The antioxidant also will react with any residual reducing agent(s) to suppress unwanted polymerization of DCPD during the distillation process step.

Examples of suitable antioxidants are phenol based compounds such as 4,4'-dioxydiphenyl, hydroquinone monobenzyl ether, 2,4-dimethyl-6-t-butylphenol, 2,6-di-t-butylphenol, 2,6-di-t-amylhydroquinone, 2,6-d-t-butyl-p-cresol, 4-hydroxymethyl-2,6-di-t-butylphenol, 4,4'-methylene-bis-(6-t-butyl-o-cresol), butyl hydroxyl anisole, phenol condensates, butylenephenol, dialkylphenolsulfide, high molecular weight polyfunctional phenols, bisphenol, and the like. Quinone based antioxidants also can be utilized. Suitable examples include butylcatechol, hydroquinone, resorcin, pyrogallol, and the like. Among these, 2,6-di-t-butylphenol, 2,4-dimethyl-6-t-butylphenol, which are sublimating compounds, are preferred since they also provide an antioxidant for the gaseous components in the distillation column.

The antioxidants can be used singly or as a mixture of two or more. The amount of antioxidant employed must be at least 100 ppm (based on DCPD after mixing with the reducing agent), preferably about 200 to about 10,000 ppm.

The activated DCPD composition thus obtained is at least 96 weight % pure, containing only trace amounts of metathesis polymerization inhibiting components.

Dicyclopentadiene Polymer Manufacture

The highly polymerizable DCPD obtained by the abovedescribed process is able to bulk polymerize to a DCPD polymer in the presence of a metathesis catalyst. The bulk polymerization of activated monomer preferably is conducted in a mold by the RIM method.

In case the treated DCPD contains trace amounts of polymerization inhibitors, the activated DCPD monomer preferably is used following treatment.

The highly polymerizable DCPD so obtained can be polymerized as a single monomeric component, or can be polymerized with at least one other copolymerizable cycloolefin comonomer. Examples of suitable comonomers include other norbornene type monomers selected from bicyclic monomers such as norbornene, norbornadiene and the like; tricyclic monomers such as substituted dicyclopentadiene, dihydrodicyclopentadiene, and the like, tetracyclic monomers such as tetracyclododecene, and the like; pentacyclic monomers such as tricyclopentadiene, and the like; heptacyclic monomers such as tetradicyclopentadiene, and the like. The alkyl substituted derivatives (e.g., methyl, ethyl, propyl, butyl substituents and the like); alkylidene substituted derivatives (e.g., ethylidene substituents and the like); aryl substituted derivatives (e.g., phenyl, tolyl, naphthyl substituents, and the like); and polar derivatives such as ester, ether, cyano, and halogen substituents, and the like of the foregoing monomer types are also within the scope of this invention.

A monocycloolefin such as cyclobutene, cyclopentene, cyclopentadiene, cyclooctene, cyclododecene, and the like may be mixed with the foregoing monomers, provided that the properties of the resulting polymer are not impaired.

Catalyst System

Any known metathesis catalyst suitable for the ring-opening polymerization of norbornene type monomers can be employed in this invention (see, for example, Japanese Kokai application Nos. 58-127728, 58-129013, 59-51911, 60-79035, 60-186511, and 61-126115).

Examples of suitable metathesis catalysts are the halides, oxyhalides, oxides, organic ammonium salts of tungsten, molybdenum, tantalum, and the like. Examples of suitable cocatalysts are alkylaluminum halides, alkoxyalkylaluminum halides, aryloxyalkylaluminum halides, organotin compounds, and the like.

In addition to the catalyst and cocatalyst, an activating agent can be employed as disclosed in Japanese Kokai application No. 60-79035. Halohydrocarbons such as chloroform, carbon tetrachloride, hexachloropentadiene, or metal halides such as silicon tetrachloride, germanium tetrachloride, and lead tetrachloride can be used as activating agents.

The amount of the metathesis catalyst employed ranges from about 0.01 to about 50 mmoles, preferably about 0.1 to about 10 mmoles per mole of norbornene based monomer utilized. The amount of cocatalyst utilized ranges from about 0.1 to about 200 molar ratio based on the catalyst component, preferably in the 2 to 10 (molar ratio) range.

Preferably, the metathesis catalyst and cocatalyst are dissolved in the monomer. So long as product quality is not adversely affected, the catalyst and/or cocatalyst can be suspended or dissolved in an inert solvent before introduction into the monomer.

Additives

Additives such as antioxidants, filler materials, reinforcing materials, pigments, coloring agents, foaming agents, flame retardants, lubricants, elastomers, and/or dicyclopentadiene type hydrogenated thermopolymer resins can be added to the monomer composition to enhance the properties of the polymer product. The additives can be added to either one or both reactant solutions, or may be added to a third reactant solution.

Suitable antioxidants include phenolic, phosphorus, or amine type compounds that are commonly used in plastics and rubbers.

Suitable fillers include inorganic materials such as milled glass, long glass fibers, glass mat, carbon black, talc, calcium carbonate, mica, and the like.

Suitable reinforcing materials include fibrous fillers such as glass and carbon fibers and the like.

Suitable foaming agents include liquid, readily volatilizable, low boiling organic compounds such as hydrocarbons selected from pentane or hexane; halohydrocarbons such as methylene chloride, trichlorofluoromethane, dichlorodifluoromethane, and the like; or an inert gas such as nitrogen or argon.

Suitable elastomers include natural rubber, polybutadiene, polyisoprene, styrene-butadiene copolymer (SBR), styrene-butadiene-styrene block copolymer (SBS), styrene-isoprene-styrene block copolymer (SIS), ethylene-propylene-diene terpolymer (EPDM), ethylene-vinyl acetate copolymer (EVA), and their hydrogenated derivatives.

In molding articles from the activated monomer compositions of the present invention, reaction injection molding (RIM) is preferred. In a preferred RIM process, a norbornene type monomer solution is divided into two portions and placed into two separate containers. A metathesis catalyst is added to one of the containers and a cocatalyst is added to the other container to yield two stable reactant compositions. The compositions are stored under inert atmospheric conditions. In the molding operation, the two reactant compositions, i.e., low viscosity solutions, are mixed to obtain a reactive polymerization feed composition that is conveyed to a mold of a desired configuration where the polymerization is carried out (i.e., the reactant streams are conveyed to the head of an impingement mixing device and instantly mixed). The reaction composition or solution is injected into a preheated RIM mold and bulk polymerized to obtain an in-mold polymerized product. This invention is not limited to two reactant streams in that additional reactant streams can be provided for the addition of other components to the reactive feed solution. The additives can be added to either one or both reactant solutions, or may be added to a third reactant solution.

Besides an impingement mixer, a dynamic or static mixer be employed as low pressure feeders. After mixing, the reactive solution can be conveyed (e.g., poured or injected) into a preheated mold in several portions (batch feeding) as disclosed in Japanese Kokai application No. 59-51911 and U.S. Pat. No. 4,426,502. Alternatively, the reactive solution can be injected in a continuous mode.

The apparatus utilized in the latter embodiment is compact in comparison to an impingement mixing device. Additionally, the latter devices can be operated under lower pressure parameters. Furthermore, the injection rate can be lowered when utilizing large amounts of filler materials, allowing the homogeneous impregnation of reaction solution into the filler materials.

The mold cavity can be filled with an inert gas atmosphere (such as nitrogen) but this is not necessary for operation of the invention. Generally, the mold pressure in the range of about 0.1 to about 10 kg/cm$^2$, and more preferably about 5 kg/cm$^2$ is employed. The mold temperature employed ranges from about 10° to about 150° C., preferably about 30° to about 100° C.

The polymerization time can be selected individually but is generally less than 20 minutes and, preferably, about 5 minutes or less.

The following examples will show one skilled in the art how to operate within the scope of the present invention and are not intended to serve as a limitation on the scope thereof. In these examples all parts are expressed as parts by weight and all percentages are expressed as percentages by weight, unless otherwise indicated.

EXAMPLE 1

Crude DCPD (94.0% purity) containing endo- and exo-isomers, 0.1% cyclopentadiene, trace amounts of hydrocarbons with 4 to 6 carbons, 5.79% methylbicyclonorbornadiene codimers such as vinylnorbornene and propenylnorbornene, 0.06% oxygen-containing inhibitors and 0.05% 5-propyne-2-norbornene was subjected to the treatment of the present invention.

The content of oxygen-containing inhibitors was determined by mixing a solution containing ferrous ion and the crude DCPD. The resulting ferric ion formed by oxygen-containing compounds was reacted with potassium thiocyanate to form ferric thiocyanate which was then titrated with titanium trichloride solution.

Two liters of the crude DCPD composition was charged into a 3 L separatory flask equipped with a stirrer. 20 ml of 15% n-butyllithium in n-hexane was then added. The solution was heated to 80° C. and stirred vigorously for one hour.

Subsequently, BHT (2,6-di-t-butyl-4-methylphenol) was added to the solution to give a 1,000 ppm antioxidant concentration. The composition was charged into a glass distillation column (30 cm long) packed with glass Raschig rings. The bottoms temperature of the column was 80° C. and the solution was flash-distilled at −700 mmHg. Although non-essential to the operation of the invention, the first 4% of the distilled fraction was discarded and 80% of the main fraction was collected. The purity of DCPD was 96.1%.

The resulting highly polymerizable DCPD solution was divided into two equal portions. Into one portion were added diethylaluminum chloride, n-propyl alcohol, and silicon tetrachloride to achieve 41, 47 and 10 mmolar concentrations (based on DCPD), respectively. Into the other portion, tri(tridecyl) ammonium molybdate was added to give a 4.0 mmole concentration (based on DCPD).

The two reactant compositions were mixed in a power mixer and injected into a preheated mold (mold wall temperature of 65° C.) and allowed to polymerize. Two and one-half minutes after injection (i.e., induction) the exotherm temperature of the resin in the mold reached 160° C. The mold was cooled and opened, and the resulting DCPD polymer had a glass transition temperature ($T_g$) of 141° C.

EXAMPLE 2 to 7

The reducing agents shown in Table 1 were used and the same procedure was carried out as set forth in Example 1.

The DCPD obtained was in the 96.0–97.0% range and showed high polymerization activity DCPD polymers with excellent physical properties were obtained.

TABLE 1

| Examples | 2 | 3 | 4 | 5 | 6 | 7 |
|---|---|---|---|---|---|---|
| Type of reducing agents | Ethylmagnesium bromide | Isopropylmagnesium bromide | Hydrogen lithium aluminum | Diethylaluminum chloride | n-Butyl lithium | Diethylzinc |
| Reducing Agent Solvent | Tetrahydrofuran | Toluene | None | DCPD | n-Hexane | None |
| Concentration (%) | 10 | 10 | — | 2 | 18 | — |
| Amount of reducing agent (solution added to 2 L of crude DCPD ml) | 30 | 30 | 3 | 40 | 10 | 3 |
| Induction Time (minutes) | 2.0 | 1.8 | 2.5 | 4.5 | 3.5 | 2.5 |
| Exotherm temperature (°C.) | 180 | 165 | 155 | 157 | 150 | 155 |
| Tg of polymer (°C.) | 147 | 149 | 137 | 140 | 135 | 139 |

EXAMPLE 8

For comparison, the crude DCPD (without a reducing agent) used in Example 1 was used and polymerized in a mold in the presence of a metathesis catalyst by the same procedure. The mold was held at 80° C. and the solution was allowed to react for one hour. After the reaction, the mold was opened. The product obtained was a pudding-like mass.

EXAMPLE 9

99.1% crude DCPD, containing 0.1% cyclopentadiene, 0.8% codimer, 20 ppm oxygen-containing inhibitors and 200 ppm 5-propyne-2norbornene was subjected to the method of the present invention.

99.1% crude DCPD was mixed with 0.2 ml triethylaluminum as a reducing agent and the mixture was stirred for one hour at 70° C. The DCPD solution was allowed to cool to room temperature and was divided into two equal portions. To one portion diethylaluminum chloride, n-propyl alcohol, and silicon tetrachloride were added to obtain a 41, 47 and 10 mmolar concentration, respectively, in DCPD. Into the other portion was added tri(tridecyl) ammonium molybdate to give a 4.0 mmolar concentration in DCPD.

The two reactant solutions were mixed and injected into a mold in the same manner as set forth in Example 1. The induction time was 2.0 minutes, with an exotherm temperature of 175° C. The resulting polymer had a $T_g$ of 147° C.

EXAMPLE 10

The crude DCPD of Example 9 (without reducing agent) was divided into two portions. Proceeding according to the method of Example 9, various catalysts and cocatalysts were added to the crude DCPD and allowed to polymerize in the mold. Induction times in the order of 8 minutes and exotherm temperatures of about 80° C. were observed. The resulting polymers were rubber-like and were of no practical use.

What is claimed is:

1. A metathesis polymerizable composition comprising activated dicyclopentadiene, wherein said activated dicyclopentadiene is obtained by contacting crude dicyclopentadiene containing metathesis polymerization inhibitors with at least one reducing agent and reacting said reducing agent with said polymerization inhibitors for about 10 minutes to about 2 hours at a temperature ranging from about 30° to about 120° C., wherein the reaction products of said reducing agent(s) and said metathesis polymerization inhibitors are not removed from the metathesis polymerizable composition and wherein said reducing agent is selected from the group consisting of lithium, sodium, metal hydrides selected from lithium hydride, sodium hydride, lithium aluminum hydride, organoalkali metal compounds selected from methyllithium, ethyllithium, n-propyllithium, n-butyllithium, sec-butyllithium, cyclohexyllithium, phenyllithium, benzyllithium, phenylsodium, benzylsodium, naphthalenesodium, triphenylmethylsodium, phenylpotassium, butadienepotassium, styrenepotassium, naphthalenepotassium, cyclopentadienylsodium, lithium enolate, sodium enolate, Group IIIA organometal compounds selected from triethylboron, trimethylaluminum, triethylaluminum, triisobutylaluminum, tricyclohexylaluminum, ethylaluminum sesquichloride, ethylaluminum dichloride, diethylethoxyaluminum, Group IVA organic compounds selected from tetraethyl silicate, triethyl hydrogen silicate, hydrogen tributyltin, dibutyllead, Grignard reagents selected from methylmagnesium chloride, ethylmagnesium chloride, ethylmagnesium bromide, n-butylmagnesium chloride, butylmagnesium iodide, phenylmagnesium chloride, vinylmagnesium chloride, arylmagnesium chloride, and compounds selected from diethylmagnesium, dibutylmagnesium, dimethylzinc, diethylzinc, dibutylzinc, methylzinc iodide, ethylzinc iodide, n-propylzinc iodide, dimethylcadmium, diethylcadmium, bidutylcadmium, diphenylcadmium, and mixtures thereof.

2. The composition of claim 1 further comprising another metathesis polymerizable cycloolefin.

3. The composition of claims 2 wherein the cycloolefin is a norbornene monomer selected from the group consisting of norbornene, norbornadiene, dihydrodicyclopentadiene, tetracyclododecene, tricyclopentadiene, tetracyclopentadiene, and mixtures thereof, and the alkyl, alkylidene, aryl, and polar derivatives thereof.

4. The composition of claim 1 wherein the reducing agent is selected from the group consisting of diethylzinc, Grignard reagents, n-butyllithium, and mixtures thereof.

5. The composition of claim 1 further comprising a component of a metathesis catalyst system selected from the group consisting of a metathesis catalyst, or a metathesis cocatalyst, and mixtures thereof with the proviso that when a metathesis catalyst is present, the reducing agent is selected from a compound that will not activate the catalyst.

6. The composition of claim 5 wherein said metathesis catalyst component is selected from the group consisting of the halides, oxyhalides, oxides, or organic ammonium salts of tungsten or molybdenum.

7. The composition of claim 5 wherein said metathesis cocatalyst is selected from the group consisting of alkylaluminum halides, alkoxyalkylaluminum halides, aryloxyalkylaluminum halides, and organotin compounds.

8. The composition of claim 6 wherein said metathesis catalyst is tri(tridecyl) ammonium molybdate, and said metathesis cocatalyst is diethylaluminum chloride.

9. A process for the preparation of dicyclopentadiene having high polymerization activity comprising dispersing at least one reducing agent within crude dicyclopentadiene containing metathesis polymerization inhibitors and reacting said reducing agent with said polymerization inhibitors under suitable reaction conditions by mixing the crude dicyclopentadiene and the reducing agent from about 10 minutes to about 2 hours at a temperature ranging from about 30° to about 120° C., and optionally separating the reaction products from the dicyclopentadiene composition, to obtain a metathesis polymerizable dicyclopentadiene composition.

10. The process of claim 9 wherein the reducing agent is selected from the group consisting of alkali metals, metal hydrides, organoalkali compounds, Group IIIA organometal compounds, Group IVA organic compounds, Grignard reagent compounds, compounds selected from the group consisting of diethylmagnesium, dibutylmagnesium, dimethylzinc, dibutyl zinc, methylzinc iodide, ethylzinc iodide, n-propylzinc iodide, dimethyl cadmium, diethylcadmium, dibutylcadmium, diphenylcadmium, and mixtures thereof.

11. The process of claim 10 wherein the alkali metals are selected from the group consisting of lithium, sodium, and mixtures thereof; the metal hydrides are selected from the group consisting of lithium hydride, sodium hydride, lithium aluminum hydride, and mixtures thereof; the organoalkali metal compounds are selected from the group consisting of methyllithium, ethyllithium, n-propyllithium, n-butyllithium, sec-butyllithium, cyclohexyllithium, phenyllithium, benzyllithium, phenylsodium, benzylsodium, naphthalenesodium, triphenylmethylsodium, phenylpotassium, butadienepotassium, styrenepotassium, naphthalenepotassium, cyclopentadienylsodium, lithium enolate, sodium enolate, and mixtures thereof; the Group IIIA organometal compounds are selected from the group consisting of triethylboron, trimethylaluminum, triethylaluminum, triisobutylaluminum, tricyclohexylaluminum, diethylaluminum chloride, ethylaluminum sesquichloride, ethylaluminum dichloride, diethylethoxyaluminum, and mixtures thereof; the Group IVA organic compounds are selected from the group consisting of tetraethyl silicate, triethyl hydrogen silicate, hydrogen tributyltin, dibutyllead, and mixtures thereof; and the Grignard reagents are selected from the group consisting of methylmagnesium chloride, ethylmagnesium chloride, ethylmagnesium bromide, n-butylmagnesium chloride, butylmagnesium, iodide, phenylmagnesium chloride, vinylmagnesium chloride, arylmagnesium chloride, and mixtures thereof.

12. The process of claim 10 wherein the reducing agent is selected from the group consisting of diethylzinc, Grignard reagents, n-butyllithium, and mixtures thereof.

13. The process of claim 11 wherein the amount of reducing agent employed ranges from about 0.005 to about 1.0 weight % based on crude dicyclopentadiene.

14. The process of claim 9 wherein said reaction products are separated by distillation in the presence of an antioxidant.

15. The process of claim 9 wherein the dicyclopentadiene obtained from said process is bulk-polymerized in a mold via ring-opening metathesis polymerization.

* * * * *